United States Patent [19]

Abdel-Monem et al.

[11] Patent Number: 4,948,594
[45] Date of Patent: * Aug. 14, 1990

[54] COPPER COMPLEXES OF ALPHA-AMINO ACIDS THAT CONTAIN TERMINAL AMINO GROUPS, AND THEIR USE AS NUTRITIONAL SUPPLEMENTS

[75] Inventors: Mahmoud M. Abdel-Monem, Moscow, Id.; Michael D. Anderson, Minnetonka, Minn.

[73] Assignee: Zinpro Corporation, Edina, Minn.

[*] Notice: The portion of the term of this patent subsequent to Feb. 13, 2007 has been disclaimed.

[21] Appl. No.: 396,685

[22] Filed: Aug. 22, 1989

Related U.S. Application Data

[63] Continuation-in-part of Ser. No. 293,225, Jan. 3, 1989, Pat. No. 4,900,561, which is a continuation-in-part of Ser. No. 285,593, Dec. 16, 1989, abandoned.

[51] Int. Cl.$^5$ ............................................. A23L 1/304
[52] U.S. Cl. .................................. 426/2; 423/557; 423/604; 424/637; 426/74; 514/499; 556/110; 562/561; 562/562; 562/563
[58] Field of Search ............... 426/2, 74; 562/561, 562/562, 563; 556/110; 423/557, 604; 424/637; 514/499

[56] References Cited

U.S. PATENT DOCUMENTS

| | | | |
|---|---|---|---|
| 2,833,021 | 5/1958 | House | 562/562 |
| 2,833,821 | 5/1958 | Hause | 562/562 |
| 3,244,527 | 4/1966 | Baker | 426/74 |
| 3,463,858 | 8/1969 | Anderson | 424/289 |
| 3,925,433 | 12/1975 | Abdel-Monem et al. | 260/438.5 R |
| 3,928,506 | 12/1975 | Gobert | 562/561 |
| 3,941,818 | 3/1976 | Abdel-Monem | 260/429.9 |
| 3,950,372 | 4/1976 | Abdel-Monem | 260/429 R |
| 4,013,699 | 3/1977 | Passedout | 562/561 |
| 4,021,569 | 5/1977 | Abdel-Monem | 424/289 |
| 4,039,681 | 8/1977 | Abdel-Monem | 424/289 |
| 4,067,994 | 1/1978 | Anderson et al. | 424/295 |
| 4,599,152 | 7/1986 | Ashmead | 204/72 |
| 4,670,269 | 6/1987 | Abdel-Monem | 426/74 |
| 4,670,428 | 6/1987 | Sorenson | 514/499 |
| 4,678,854 | 7/1987 | Abdel-Monem | 556/149 |
| 4,764,633 | 8/1988 | Anderson | 556/50 |
| 4,786,510 | 11/1988 | Nakel | 426/74 |
| 4,786,518 | 11/1988 | Nakel | 426/74 |

FOREIGN PATENT DOCUMENTS

| | | | |
|---|---|---|---|
| 46-26353 | 7/1971 | Japan | 514/499 |
| 49-12028 | 5/1972 | Japan | 514/499 |
| 43-34205 | 10/1973 | Japan | 514/499 |

OTHER PUBLICATIONS

Lehninger, 1970, Biochemistry, Worth Publishers, Inc. pp. 69–71.
Kurtz, 1949, J. Biological Chemistry 180:1253–1267.
Roeske et al., 1956, J. American Chemical Society 78:5883–5887.

Primary Examiner—Carolyn Paden
Attorney, Agent, or Firm—Zarley, McKee, Thomte, Voorhees & Sease

[57] ABSTRACT

In solid form, copper complex salts of the formula:

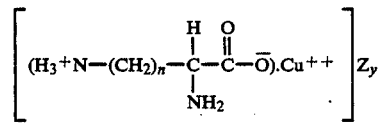

wherein "n" is from 1 to 5, and "Z" is an anion and "y" is the number required to electrostatically balance the set.

5 Claims, No Drawings

COPPER COMPLEXES OF ALPHA-AMINO ACIDS THAT CONTAIN TERMINAL AMINO GROUPS, AND THEIR USE AS NUTRITIONAL SUPPLEMENTS

CROSS REFERENCE TO A RELATED APPLICATION

This application is a continuation-in-part of Application Ser. No. 293,225 filed Jan. 3, 1989, and entitled COPPER COMPLEXES OF ALPHA-AMINO ACIDS THAT CONTAIN TERMINAL AMINO GROUPS, AND THEIR USE AS NUTRITIONAL SUPPLEMENTS now U.S. Pat. No. 4,900,561 which is a Continuation-in-part of Ser. No. 285,593 filed Dec. 16, 1989 now abandoned.

BACKGROUND OF THE INVENTION

The important physiological role of copper in vertebrates was first demonstrated in 1928. Since that time, copper was found to be a key component of several enzymes. Most of these copper-containing enzymes are known to catalyze physiologically important reactions. Dietary deficiency of copper in vertebrates results in several pathological disorders.

One early manifestation of copper deficiency is spontaneous fracture of bones in sheep and cattle that graze in copper-deficient pastures. Experimentally induced copper deficiency resulted in bone abnormalities in rabbits, pigs, chickens and dogs. The bone defect appears to reside in the organic matrix and not in the mineral make-up of the bone.

Copper deficiency results in the failure of pigmentation of hair and wool in numerous species including black-wooled correlated with copper supplementation. Feathers of turkey poults fed copper-deficient diets also show lack of pigmentation.

Copper deficiency can cause cardiac lesion in cattle which may even result in sudden death. Further, chicks and pigs fed copper-deficient diets may die suddenly from massive internal hemorrhage due to structural defects in major arteries.

Subnormal levels of copper in the forage has resulted in neonatal ataxia or swayback in lambs. Copper-deficient pigs do not absorb iron at a normal rate. It appears that copper is also essential for the release of iron from the intestinal mucosa and iron storage tissues. In general, copper deficiencies cause anemia in all the species that have been studied so far.

Only a fraction of the copper ingested in diet is ultimately utilized in the formation of copper-proteins. The form of the copper ingested influences the degree of its utilization as measured by ceruloplasmin (copper-protein enzyme) activity. The presence of some amino acids have been known to cause an increase in the absorption and utilization of copper. (Kirchgessner and Girassmann, Z. Tierphysiol. Tierenahrung Futtermittelk. 26:3 (1970; Girassmann et al., Z. Tierphsiol. Tierernahrung Futtermittelk. 28:28 (1971); Schwarz et al., ibid. 31:98 (1973).)

It can, therefore, be seen that proper dietary balance of highly bioavailable copper is important for animals, including swine and poultry. In recent times, it has been reported, particularly for swine and poultry, that they may have copper deficiencies because of the nature of their food rations. Put another way, it has been found that from time to time, mycotoxins which are present in food rations, particularly corn, have a tendency to tie up the available copper in a form which makes it non-bioavailable. Thus, the net result is that the feed for the swine and the poultry containing mycotoxins may in some way bind the available copper in the food to make it non-bioavailable. The net result is that even though one feeds to the animals much higher levels of copper than the NRC (National Research Council) recommended daily allowances, the animal does not get anywhere near its adequate NRC requirement.

An additional problem is caused by feeding high levels of copper which are simply thereafter excreted without uptake. The copper in the excretement is returned to the soil, significantly raising the copper level. This may cause undesired environmental polluting problems.

It therefore can be seen that adequate dietary levels of highly bioavailable copper are necessary for development of livestock, including cattle, swine and poultry. Moreover, there is a need to present copper in a highly bioavailable form which assures that the animal will have a high level of uptake of the copper without excreting it to cause potential environmental pollution.

It is an especially preferred advantage to make the complexes of the present invention from essential amino acids. This allows not only for increased bioavailability of the copper, but also it allows the animal a proper nutritional amount of an essential amino acid necessary for proper growth. For copper, it is especially difficult to form solid form complexes of copper and alpha-amino acids. For example, if one attempts to form such a complex with methionine in accord with the general procedures outlined in U.S. Pat. No. 3,941,818 issued Mar. 2, 1976 and U.S. Pat. No. 4,021,569 issued May 3, 1977, the result is an oxidation-reduction reaction between the methionine and the copper, resulting in an unuseable reaction product. It has now been discovered that when copper complexes of alpha-amino acids having a terminal amine group are employed, the internal redox reaction does not occur.

It is therefore a primary objective of the present invention to provide a highly effective bioavailable form of copper in convenient water soluble salt form which is available for use as a feed additive in animal nutrition.

Another important objective of the present invention is the preparation of new, complex salts of copper in which the copper is in a form that can be readily absorbed after ingestion by livestock, particularly swine, poultry and cattle.

Yet another objective of the present invention is to provide complexed salts of copper which, because of the complexing of copper with certain alpha-amino acids containing a terminal amine moiety, are shelf stable.

An even further objective of the present invention is to provide a method of nutritional supplementation for animals to assure adequate dietary requirements of copper for growth and health.

An even further objective of the present invention is to provide certain complex salts of copper and certain alpha-amino acids containing a terminal amine moiety, such as lysine, which have coordination bonds formed between the copper ion and the alpha-amino group of the acid, in addition to an electrostatic attraction bond between the cation and the carboxyl ions.

An even more specific objective of the present invention is to prepare 1:1 ratio complexes wherein the ratio of copper to the alpha-amino acid is 1:1.

The method of accomplishing these as well as other objectives of the invention will become apparent from the detailed description of the invention which follows hereinafter.

SUMMARY OF THE INVENTION

This invention relates to the preparation of copper complexes having the following general formula:

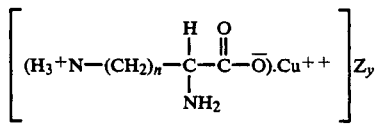

wherein "n" is from 1 to 5, and "Z" is an anion and "y" is the number required to electrostatically balance the set. Because of a complex formed between the copper and the alpha-amino acid, it is believed these compounds are in a form that is readily absorbed by domestic livestock, including cattle, swine, and poultry. These complexes thus function as a readily available source of copper for dietary supplementation while simultaneously providing essential alpha-amino acids for normal growth and health.

DETAILED DESCRIPTION OF THE INVENTION

The compounds of the present invention can be described as copper complex salts between the copper cation and certain alpha-amino acids with a terminal amine moiety of the general formula:

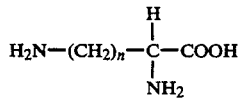

wherein "n" equals 1–5. The preferred acid is when "n" equals 4, lysine. However, "n" should not increase substantially beyond 5 because compounds for "n" greater than 5 are not readily available and not commercially feasible.

It is also important to note that the compounds of this invention are copper complexes in which coordination bonds are formed between the copper cation and the alpha-amino group of the acid, in addition to the electrostatic attraction between the cation and the carboxyl ions. This complex salt involving both coordination bonds and electrostatic attraction seems to enhance the bioavailability of the copper.

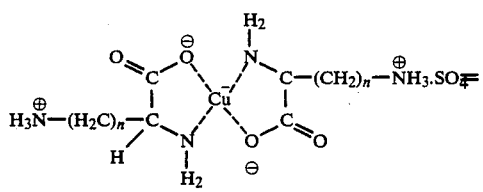

For 1:1 complexes, the formula illustrating both the coordination bond and the electrostatic attraction can be represented as follows:

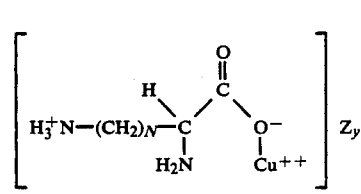

wherein "y" is a number required to electrostatically balance the salt and "Z" is an anion.

While the above formulas represent the compounds sterically, the compounds can be represented as well by the following formula:

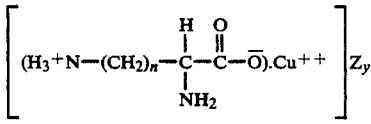

"n" is 1:5, and "Z" is an anion, and "y" is the number required to electrostatically balance the salt. It is important to remember that these salts are capable of existing in stable solid state form. They are thus processible and useable in animal feeds. This is to be distinguished from mere existence in non-isolatable transient states in an equilibrium of a solution. Preferred salts are those of the alpha-amino acid lysine wherein "n" equals 4. The most preferred salt is copper lysine sulfate either the 1:2 or the 1:1 complexes. In the formula presented, "Z" equals the anion, and may be an inorganic anion or an organic anion. Preferably, "Z" is selected from the group consisting of chloride, bromide, iodide, sulfates and phosphates. By the term "sulfates" and "phosphates" it is intended to include acid sulfates and acid phosphates, as well as those having no hydrogen moities associated with either the sulfate or the phosphate, i.e., simply the sulfate $SO_4$ —and the phosphate $PO_4^{-3}$.

For the preferred solid form copper complexes of lysine and copper chloride, or copper sulfate, the complexes are stable, very water soluble, blue crystalline materials.

The 1:1 complexes are slightly less stable but are also more economical because they consume less lysine in manufacture. Generally, 1:1 complexes will be achieved if the pH is controlled on the more acid side, for example, from about 3.0 to about 4.0. It is believed that even the more stable 1:2 complexes are converted to 1:1 complexes in the acid environment of the gut.

For details of other copper complexes of the hydroxy acids for similar uses, see co-pending and commonly assigned application for COPPER COMPLEXES OF ALPHA HYDROXY ORGANIC ACIDS AND THEIR USE AS NUTRITIONAL SUPPLEMENTS, Ser. No. 260,023, filed Oct. 20, 1988.

Simple and economically feasible processes of preparing these copper complexes have been developed. In accord with the process of this invention, a solution of the lysine monohydrate is heated to 60°–80° C. Hydrochloric acid is carefully added followed by the careful addition of copper oxide. The mixture is stirred for approximately 30 minutes. The small amount of insoluble copper oxide is removed by filtration. The filtrate is concentrated to dryness using conventional methods, such as hot air oven, spray drying, freeze drying or evaporation under reduced pressure, to give the desired product.

The same products may be obtained by carefully mixing a solution of lysine monohydrochloride with basic cupric carbonate. The mixture is heated under reflux for two hours. The solution was filtered while hot and cooled to 20° C. Acetone is added step-wise to the cooled filtrate until turbidity is observed. The mixture is stored overnight at 4° C. to precipitate the desired product. The desired product may also be obtained from the filtrate by using a conventional drying method. The desired product could be further purified by recrystallization from acetone-water.

Another convenient method for obtaining the copper complexes involves the careful addition of powdered copper sulfate to a hot solution of lysine monohydrate. The desired product is obtained from the mixture as described in the previous examples.

The formation of copper complexes of basic alpha-amino acids such as lysine, Ornithine and gamma amino butyric acid are commonly used as a means of protecting or blocking the alpha-amino group in synthetic reactions in which it is desired to derivatize the side chain amino group. (Ref. A.C. Kurtz, J. Biol. Chem., 180, 1253 (1949); R. Roeske and F.H.C. Stewart, R.J. Stedman and Vincent Du Vigneaud, J. American Chemical Society, 78, 5883 (1956).) However, the procedures used in the reactions involve small amounts of reactants and complex methods which are not applicable for the preparation of large amounts of product. Additionally, the copper complexes are not usually isolated in crystalline form and are not characterized.

A distinct advantage of the compounds of the present invention is that they are crystalline, stable and water soluble compounds which can be easily obtained in large quantities for use as feed additives at a relatively low cost. The compounds of this invention provide a readily available source of copper and the essential alpha-amino acid lysine.

The level of addition of the copper alpha-amino acids acids containing a terminal amino moiety of this invention for use as a feed supplement can vary over a wide range. Preferably, the level of addition is such to provide dietary intake of copper from about 0.2 parts per million to about 2.0 parts per million, and most preferably from about 1.0 parts per million. These levels are satisfactorily achieved when the amount of the preferred complex salt of copper lysine, including both the 1:1 and 1:2 complexes as well as others added to the animal feed, is from about 0.1 g per head of cattle per day to about 1.0 g per head of cattle per day, preferably 0.6 g per head of cattle per day. It should, however, be understood that other levels of addition can be utilized and that the precise level of addition is not, in fact, critical, it being adjusted for the conditions of the animals being treated with the nutritional supplement.

Importantly, one of the distinct advantages of the compounds of the present invention is that they are crystalline water soluble compounds easily processible and size reducible to a powder for use in a convenient feed supplement form. In other words, their physical form is one which is easily mixable with typical ruminant animal feeds.

In making nutritional supplements for addition to the diets of animals, it is preferred that the complexes of the present invention be added to carrier or filler materials for processibility, ease of handling and sale. Examples of suitable carriers include distillers fermentation solubles, feed grains, animal, poultry and fish bi-products and meal, whey and other cellulosic carrier materials well-known in the trace mineral product preparation techniques of the art.

The following example is offered to illustrate, but not limit, the preparation of the compounds of the present invention.

EXAMPLE 1

Basic cupric carbonate (12 gm.) was added portionwise very carefully to a solution of lysine monohydrochloride (10 gm.) in water (100 ml.). The mixture was heated under reflux for 2 hours. The solution was filtered while hot. The filtrate was cooled to 20° C and acetone was added stepwise until turbidity was observed. The mixture was stored at 4° C overnight. The precipitate was collected and dried. An analytical sample was prepared by recrystallization from water-acetone. The sample was dried over phosphorus pentoxide. The infrared spectrum of the product was recorded in KBr pellet and found to be compatible with the structure herein given. Elemental analysis for $C_{12} H_{28} O_4 N_4 Cl_2 Cu, 2 H_2 O$ calculated found: C, 31.14 (13.51); H, 6.96 (6.93); N, 12.10 (11.86); Cl, 15.31 (15.15). Copper analysis using ashing procedure. Ash 14.33 percent; copper calculated at 11.44 percent from ash. Theory was 13.73 percent. This elemental analysis confirms the structure of 1:2 complexes.

EXAMPLE 2

Lysine monohydrate (16.7 gm.) was mixed with water (25 ml.) and the mixture was heated with stirring at 60°–80° C. until all the solid was dissolved. Concentrated hydrochloric acid (9.8 ml. of 37.3 percent) was added very carefully. The stirring of the solution was continued during the addition of acid. Copper oxide (4.0 gm.) was added to the stirred solution and stirring was continued at 70° C for 30 minutes. The hot mixture was filtered to remove unreacted copper oxide. The filtrate was concentrated to dryness to give the desired product (21 gm.). The product is very soluble in water and gives a clear deep blue solution. The color of the solid product depends on the degree of hydration. An anhydrous product has a yellow-green color, and as the solid becomes hydrated, it changes to deep blue. The solid has the same chemical and physical properties as that of the product obtained in Example 1.

EXAMPLE 3

Lysine monohydrate (800 pounds) was mixed with 1,400 pounds of hot water. The solution was mixed until all the lysine had dissolved (approximately 10 minutes). Next, stirring was continued while copper sulfate pentahydrate (600 pounds) was slowly added.

After all the copper sulfate pentahydrate had been added to the lysine solution, stirring was continued and the solution was maintained at 160°–180° F. for 10–15 minutes to allow the complexing reaction to occur.

The copper lysine complex was dried using a conventional spray dry technique. The resulting desired product was a green fine powder.

This compound, if fed to livestock, particularly swine, cattle and poultry and also for example, sheep, at the levels specified herein, will show that the copper is in a higly bioavailable form and will provide it at levels sufficient for adequate dietary intake of copper to provide normal healthy growth, good red blood cell production, proper pigmentation for hair and wool, and at sufficient levels for normal reproductive patterns.

EXAMPLE 4

This example prepares the 1:1 copper lysine complex. For a 1:1 complex, the ratio of copper sulfate pentahydrate to lysine hydrochloride should be 1.4:1.

Lysine monohydrochloride (365 pounds) was mixed with 1200 pounds of hot water. The solution was mixed until all the lysine had dissolved (approximately 10 minutes). Next, stirring continued while copper sulfate pentahydrate (500 pounds) was slowly added.

After all the copper sulfate pentahydrate had been added to the lysine solution, stirring was continued and the solution was maintained at 160°–180° F. for 10–15 minutes to allow the complexing reaction to occur.

The copper lysine solution was dried using a conventional spray dry technique. The resulting desired product was a fine powder.

It therefore can be seen that the invention does and will accomplish all of its stated objectives.

We claim:

1. In solid form, 1:1 copper complex salts of the formula:

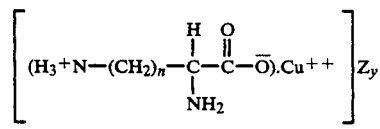

wherein "n" is from 1 to 5, and "Z" is an inorganic anion and "Y" is the number required to electrostatically balance the set.

2. The cooper complexes of claim 1 wherein "Z" is selected from the group consisting of chloride, bromide, iodide, sulfates and phosphates.

3. A method of assuring adequate dietary requirement of bioavailable copper for good growth and yield production of livestock, said method comprising: adding as a feed ration supplement to the animal's feed, a small but effective amount of a 1:1 copper complex salt of the formula:

$$\left[ (H_3{}^+N-(CH_2)_n-\underset{\underset{NH_2}{|}}{\overset{\overset{H}{|}}{C}}-\overset{\overset{O}{\|}}{C}-\overline{O}).Cu^{++} \right] Z_y$$

wherein "n" is from 1to 5, and "Z" is an inorganic anion, and "Y" is the number required to electrostatically balance the set.

4. The method of claim 3 wherein the amount of said salt added to the animal's diet is from 0.1 to 1.0 g per head per day.

5. 1:1 copper lysine sulfate.

* * * * *